United States Patent [19]

Rodabaugh et al.

[11] Patent Number: 5,175,502
[45] Date of Patent: Dec. 29, 1992

[54] METHOD AND APPARATUS FOR DETERMINING ACID CONCENTRATION

[75] Inventors: Ronald D. Rodabaugh, Middletown; Franklin E. Rower, Monroe, both of Ohio

[73] Assignee: Armco Steel Company, L.P., Middletown, Ohio

[21] Appl. No.: 583,054

[22] Filed: Sep. 14, 1990

[51] Int. Cl.⁵ ............................................. G01N 27/02
[52] U.S. Cl. ................................. 324/439; 324/438; 324/441; 134/10
[58] Field of Search ............... 324/425, 438, 439, 441, 324/444, 446; 134/113, 64 R, 10; 204/408, 409, 433; 156/626, 627

[56] References Cited

U.S. PATENT DOCUMENTS

| | | | |
|---|---|---|---|
| 3,062,223 | 11/1962 | Malin et al. | 134/57 |
| 3,074,277 | 1/1963 | Hill | 73/439 |
| 3,262,051 | 7/1966 | Payne, Jr. | 324/29 |
| 3,427,198 | 2/1969 | Hill | 134/10 |
| 3,433,670 | 3/1969 | Hill | 134/10 |
| 3,669,623 | 6/1972 | Allison et al. | 23/154 |
| 4,233,106 | 11/1980 | Goffredo | 134/10 |

Primary Examiner—Jack B. Harvey
Attorney, Agent, or Firm—Larry A. Fillnow; Robert J. Bunyard; Robert H. Johnson

[57] ABSTRACT

Acid concentrations are determined by the method and apparatus, particularly HCl acid for picking ferrous material. Specific gravity measurements are made on acid samples, diluted acid samples and water. Conductivity measurements are conducted on the diluted acid samples. The water dilution minimizes the influence of the metal salt in the sample to improve the conductivity measurements. The system calculates the acid concentration by a series of approximations using the conductivity data and the acid concentration - conductivity relationships to provide an accurate acid concentration which is easily automated by computer.

19 Claims, 3 Drawing Sheets

METHOD AND APPARATUS FOR DETERMINING ACID CONCENTRATION

FIELD OF THE INVENTION

The present invention relates to acid analysis and more particularly the analysis of hydrochloric acid. The invention is directed to the pickling of steel and the control of acid concentrations in the pickle liquor.

BACKGROUND OF THE INVENTION

Pickling is the process of chemically removing oxides and scale from the surface of a metal by the use of acids such as sulfuric, nitric, hydrochloric and hydrofluoric. The reaction between the metal being treated and the acid also includes the solution of metal as a salt of the acid and the evolution of hydrogen.

The rate of pickling is affected by the acid concentration, temperature and time of metal immersion. The nature of the metal oxide present, such as $FeO$, $Fe_2O_3$ or $Fe_3O_4$, will also influence the rate of pickling.

Since the acid in the pickling operation is gradually consumed by the removal of the oxides and scale, additional fresh acid is added along with water to maintain a uniform cleaning operation. The acid in the pickling tanks is therefore regularly monitored and maintained within relatively critical levels.

In this regard, various measuring systems for controlling pickling conditions and measuring acid concentrations have been used.

U.S. Pat. No. 3,062,223 relates to sulfuric acid measurements and uses a controller connected to a conductivity probe having temperature compensation. Changes in acid concentration modify the conductivity of the bath. It was found that an increase in ferrous sulfate in the pickle liquor caused a rise in the bath density and a drop in bath temperature also caused an increase in density. The decomposition of the acid which formed ferrous sulfate influenced the conductivity readings and so did the temperature changes. Since the monitors could not determine if the temperature had dropped or if there had been an increase in ferrous sulfate, the temperature was controlled. It was critical to the process to determine if part of the bath needed to be bled off to remove ferrous sulfate or fresh acid of higher concentration needed to be added with the appropriate dilution in water. To understand which changes in bath conditions were affecting bath density and conductivity, the temperature was maintained relatively constant.

U.S. Pat. No. 3,074,277 discusses an automatic control system for sulfuric acid pickling. The system involves the independent measurement of specific gravity and ferrous sulfate concentration and combines the signals to correct the specific gravity for the component contributed by the ferrous sulfate. A net signal is obtained which is a measure of the acid concentration and can be used to control the addition of makeup acid.

U.S. Pat. No. 3,262,051 discloses a system which determines the concentration of nitric acid in a bath by using current density measurements. The voltage across a pair of electrodes disposed within a bath with a selected current density through the bath provides a strong signal for a small change in acid concentration. Slight corrections for salt formation are made in the current density if the bath is originally salt-free.

U.S. Pat. No. 3,427,198 is an improvement to U.S. Pat. No. 3,074,277 and teaches a system that maintains the ferrous sulfate constant so that the specific gravity measurement is directly proportional to the acid concentration. The ferrous sulfate is held constant by water additions using a colorimeter to determine the metal ion concentration. Hydrochloric acid pickling is also described with the ferrous chloride held constant.

U.S. Pat. No. 3,433,670 describes an automatic pickling analysis system for several acids including hydrochloric acid. A colorimeter system measures the color absorption of the ferrous salts in the acid bath. The specific gravity, with compensation for the ferrous salt, is also determined.

Prior acid analyzing systems have also included titration means for determining acid concentrations in pickling operation. However, these means are difficult to standardize and do not provide a system which is simple and easily adapted into an automatic control system.

The patents discussed above have noted that the presence of the iron salt in the pickle liquor complicates the determination of acid concentration. Various analytical approaches have included holding the salt constant, holding the temperature constant and correction for the readings. The present invention has discovered a system which is far easier to control by computer and automatically produces reliable and consistent measurements of the acid concentrations. The present invention is the first to recognize that the influence of metal salt on conductivity measurements may be minimized by using a controlled concentration of acid.

BRIEF SUMMARY OF THE INVENTION

The present invention provides a method and apparatus for measuring pickling acid concentration which includes correction in the measurements for the base metal salt present in the pickle liquor. The analyzer, in the case of hydrochloric acid pickling, measures the specific gravity of undiluted pickle liquor and then dilutes the pickle liquor for conductivity measurements. After dilution, the dependence of conductivity on the iron chloride concentration is greatly reduced and the hydrochloric acid measurement is far more accurate. The conductivity readings are corrected for temperature. The results from the analyzer are used to regulate the flow of acid into the pickling tanks.

It is a principle object of the present invention to provide an improved automatic analysis system which is simple to operate and provides a high degree of accuracy in acid measurements.

Another object of the present invention is to provide an analysis system which requires minimal calibration and needs few standardizing chemicals.

Another object of the present invention is to provide an analysis system which can be used in automatic acid addition systems.

An advantage of the present analysis system is the ability to make accurate acid determinations with equipment that is easy to maintain and operate.

Another advantage of the present invention is the improved life of the equipment resulting from dilution of the acid which reduces the equipment corrosion.

The above and other objects, advantages and features of the invention will become apparent upon consideration of the detailed description and appended drawings.

DETAILED DESCRIPTION OF THE PREFERRED EMBODIMENT

The pickling of ferrous material, which could be strip, sheet, wire or other article forms, requires the relatively precise control of acid concentrations and temperatures to insure a clean ferrous surface is provided. To maintain high production speeds, the temperature of the acids are elevated to increase pickling efficiency. It is well known to provide a continuous sample stream of pickle liquor from the pickling tanks which is pumped to the analyzing system. Various filters or baffling devices which are well known may also be used to insure the sample stream has minimal suspended particles. The removal of hydrogen or other dissolved gases may also be required by filtering to avoid an adverse influence on specific gravity measurements depending on the measuring system used. U.S. Pat. No. 3,427,198 is incorporated by reference as teaching various sampling and filtering means to provide a representative pickling solution for analysis.

Figure 1:
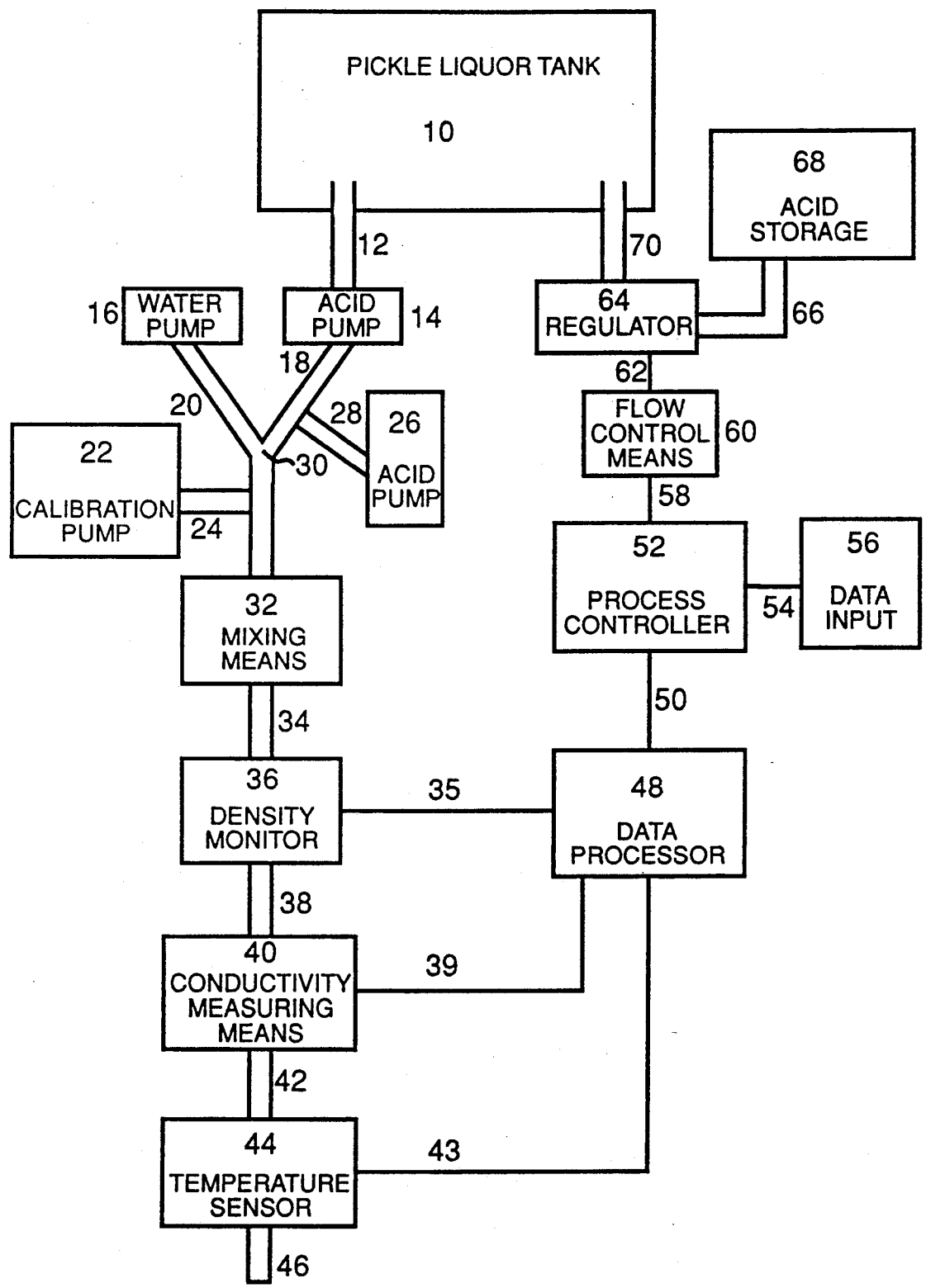
FIG. 1 is a block diagram flow chart of the present invention illustrating the sequence of measurements in determining acid concentrations.

The concentration of acid and metal salt are determined by measuring the specific gravity of the undiluted pickle liquor in tank 10 as shown in FIG. 1. Before the specific gravity is measured, the pickle liquor flows through line 12 and pumped by acid pumping means 14 into liquor line 18 where the acid flows into feed line 30. Water is supplied to pumping means 16 by means not shown and flows through water line 20 into feed line 30. Feed line 30 may contain pickle liquor, diluted pickle liquor or water depending on the stage of pickle liquor analysis. Connected to feed line 30 is mixing means 32 which provides uniform temperature and homogeneity. The temperature may be regulated by using a water bath at room temperature through which an enclosed sample line extends (not shown). The sample uniformity may be obtained by using a series of loops formed by tubing or other mixing devices. Acid metering pump 14 also serves to regulate the flow during analysis and may stop acid flow altogether as explained later.

A calibration solution pump 22 and calibration line 24 may also be provided for metering a calibration fluid used for standardizing the analyzing system during occasional checks. Additional pumping means 26 and auxiliary line 28 may be included to allow the analyzing system to be used with other pickling tanks not shown.

Specific gravity may be determined by various density instruments 36 of well known types, such as a flow through density transmitter or a differential pressure type transmitter. Line 34 provides the sample flow to the density monitor 36. Other density monitoring means may include a beta gage, a tuning fork or a weighing scale. The results from the density measurements are sent to a data processing unit 48 by signal transferring means 35.

The electrical conductivity is then measured by means 40 using a sample diluted with water from line 20 and regulated by water pump 16. Typically at least about 50% water by volume is added and preferably the acid sample is diluted by 2 to 3 times in water. The acid pump 14 and water pump 16 are computer controlled to provide an automatic system for acid analysis. With both pumps 14 and 16 operating and proportioned for proper dilution, the conductivity meter 40 is filled with a diluted acid sample and the measurements are sent to the data processing unit 48 by line 39.

The dilution of the pickle liquor sample for conductivity measurements is extremely critical to the overall accuracy of the acid measurements. Dilution reduces the effect of iron chloride on sample conductivity and allows very accurate measurements of acid concentration from the conductivity reading. Dilution fluids other than water may be used.

Figure 2:
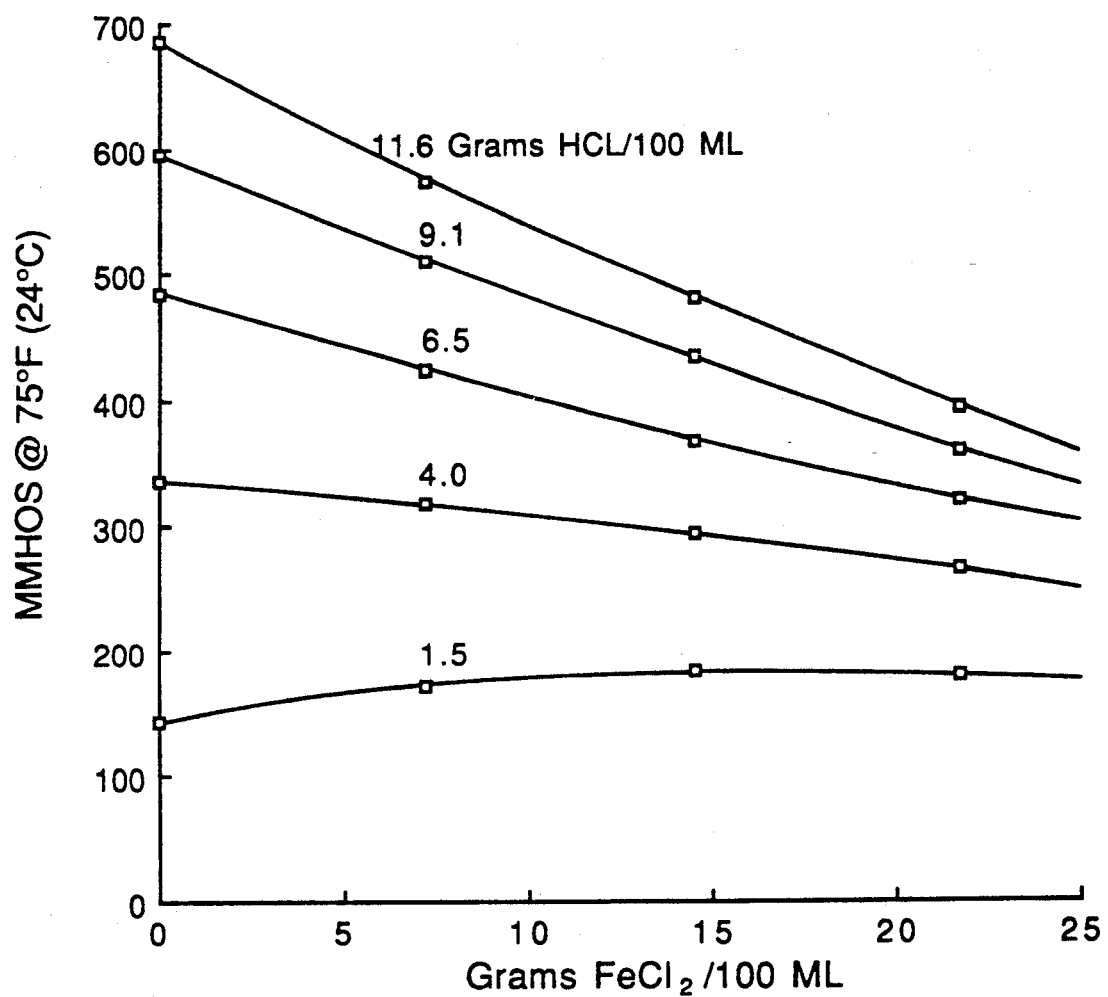
FIG. 2 shows graphically the influence of iron chloride content on the conductivity measurements when the HCl acid is not diluted.

Referring to FIG. 2, the influence of iron chloride on conductivity measurements of undiluted HCl pickle liquor at 75° F. (24° C.) is shown for various levels of iron chloride and various acid concentrations. Since most HCl pickling requires acid concentrations above 5% and typically about 10%, a slight change in iron chloride levels has drastic influence on the conductivity measurements.

Figure 3:
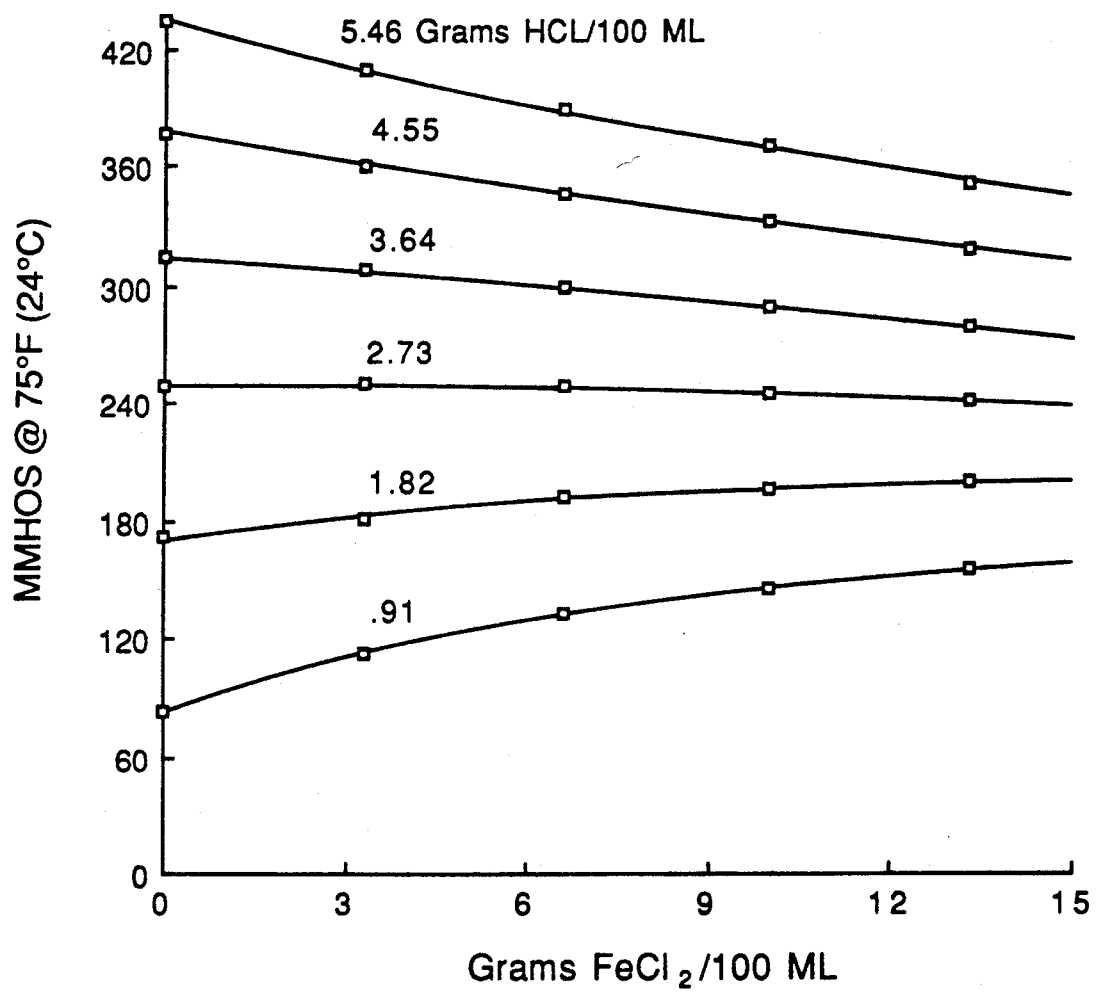
FIG. 3 shows graphically the influence of iron chloride content on the conductivity measurements when the HCl acid is diluted.

Referring to FIG. 3, the dilution effect on conductivity readings at 75° F. (24° C.) is clearly shown. By adding sufficient water, the curve can be flattened to the extent that iron chloride does not significantly influence the conductivity reading. The analysis of acid is easier to control automatically by controlling dilution of the sample rather than trying to maintain iron chloride constant of providing additional means to measure the iron chloride and making corrections to the conductivity readings. Thus, the conductivity measurements can be used to measure acid content directly with minimal compensation for iron chloride if the acid concentration level is selected properly.

It is readily apparent from FIG. 3 that a dilution of acid which produces a concentration of about 2.75 grams HCl per 100 ml of sample results in a curve which is approximately flat and the conductivity measurements are minimally influenced by the level of iron chlorides. Depending on the degree of accuracy required, a dilution to between about 1.5 and 4.5 grams HCl per 100 ml of diluted sample will provide an accurate conductivity reading which may be used to analyze the pickle liquor. A preferred range of dilution is about 1.5 to about 4 grams HCl per 100 ml of diluted sample and more preferably about 2 to about 3 grams HCl per 100 ml of diluted sample. The acid is typically diluted by adding about 1 to 2 parts water for each part acid on a volume basis. Depending on the initial acid concentration, a minimum water dilution of at least 1:1 by volume and preferably at least 2:1 by volume is used for normal pickling acid concentrations. The means to control dilution are easily regulated using this general relationship with the starting acid concentration to obtain the desired diluted range of acid.

The temperature of the acid sample is determined by sensor means 44 and the results are sent to the data processing unit 48 by line 43. The temperature may also be determined by the conductivity monitor with the appropriate temperature sensor added. This would eliminate the need for additional means 44 for temperature measurements.

The results from the density monitor, the conductivity monitor and the temperature monitor are processed by the data processor unit 48 to provide a signal indicating the concentration of acid present in the liquor. Other process controllers, not shown, may be fed by data processor 48 to regulate acid additions in other tanks. This signal is sent to a process controller 52 which is used to regulate the addition of acid and water and control the bath temperature, if necessary. Additional data input from means 56 may be sent to controller 52 which relates to changes in the substrate widths, line speeds and other process variables. The processed signal from all of the variables monitored is sent through line 58 to a flow control means 60 which determines the position of the regulation means 64 through line 62. Acid from storage means 68 is pumped through line 66 and regulating means 64 adjusts the acid flow to the pickling tank 10 through line 70.

The analyzing system may be used to measure both the % HCl and the % $FeCl_2$ if desired for more complete information on the pickle liquor. The amount of $FeCl_2$ may be calculated from the density measurements after correcting the density measurement for the contribution of HCl to the density.

The improved efficiency of the pickling analysis system of the present invention has provided automatic control features having several advantages over other systems as evidenced by the following examples. Table 1 shows the relationship between acid dilution and the influence of $FeCl_2$ on the acid measurements at about 75° F. (24° C.). The conductivity measurements were corrected for any slight deviations in temperature and acid concentrations. Table 1 shows the conductivity measurements are minimally influenced by the amount of iron chloride at about 2.73 grams HCl per 100 ml of solution. The conductivity values at 1.82 and 3.64 grams HCl per 100 ml of solution are also relatively stable over a wide range of iron chloride. When the acid concentration is much outside these ranges, the iron chloride has a stronger influence on the conductivity readings and larger corrections for the effect of $FeCl_2$ on conductivity must be applied to accurately determine the acid concentration. However, such corrections are not prohibitive and are easily applied within the range of about 1.5 to 4.5 grams HCl per 100 ml of solution. Other single acid measurement systems may also have the acid concentration diluted to a desired range where the salt formed from the reaction between the acid and the substrate does not drastically influence the conductivity measurements.

The density measurements were conducted by weighing a fixed volume of acid sample and then weighing the same volume of diluted sample and the same volume of water.

TABLE 1

| | CONDUCTIVITY (mmho) | | | | | |
|---|---|---|---|---|---|---|
| | % HCl | | | | | |
| % $FeCl_2$ | 0.91 | 1.82 | 2.73 | 3.64 | 4.55 | 5.46 |
| 0.00 | 9.3 | 17.3 | 24.7 | 31.5 | 37.7 | 43.3 |
| 3.34 | 11.3 | 18.3 | 24.9 | 30.8 | 36.2 | 40.9 |
| 6.68 | 13.2 | 19.3 | 24.8 | 30.0 | 34.7 | 39.0 |
| 10.02 | 14.6 | 19.7 | 24.5 | 29.1 | 33.3 | 37.0 |
| 13.36 | 15.5 | 19.9 | 24.3 | 28.1 | 31.8 | 35.1 |

% $FeCl_2$ and % HCl are grams per 100 ml of solution
All conductivity measurements corrected to 75° F. (24° C.)

TABLE 2

| | A, B and C COEFFICIENTS | | |
|---|---|---|---|
| % $FeCl_2$ | A COEFFICIENT | B COEFFICIENT | C COEFFICIENT |
| 0.00 | 0.02740 | 0.08785 | 0.000862 |
| 3.34 | −0.2172 | 0.08685 | 0.001258 |
| 6.68 | −0.6648 | 0.1007 | 0.001438 |
| 10.02 | −1.120 | 0.1156 | 0.001667 |
| 13.36 | −1.449 | 0.1186 | 0.002218 |

From TABLE 1 where % HCl = A + B (CONDUCTIVITY) + C (CONDUCTIVITY)$^2$ derived from a quadratic fit from conductivity data for a given % $FeCl_2$.

HCl pickle liquor was supplied to an analyzer of the present invention using metering pumps to regulate liquor and water supply. The operating cycle had the water pump shut off at the start of the process and the pickle liquor was pumped to a balance coil which was filled with the liquor. After the balance weight was read, the water pump was turned on with the acid pump to provide a dilution which brought the acid concentration into the general desired range. For an acid pickling process using an acid concentration of about 10%, a typical dilution ratio would be about 2 parts water to 1 part acid on a volume basis.

The balance coil and conductivity cell were filled with the diluted liquor. Measurements were made on the weight of the balance coil, the electrical conductivity and the temperature. The acid pump was then turned off and only water pumped through the system. The weight of the balance coil was read. The 3 balance weights, temperature, and conductivity were used to calculate the concentration of HCl and $FeCl_2$ as follows:

A sample of HCl had a conductivity reading of 27.8 mmho at 74° F. (23.3° C.). The weight of undiluted acid liquor W1 was 4.59 grams and the weight of diluted acid liquor W2 was 1.83 grams. The weight of water W3 was 0.16 grams. The dilution factor is equal to (W1−W3)/(W2−W3) which is 2.65. Using these measurements, the following calculations were determined:

1. The conductivity reading was corrected to 75° F. (24° C.) using the relationship of [conductivity measurement]$\times[1.01^{(75° F.-74° F.)}]$ which gave a corrected conductivity of 28.08 mmho.

2. The acid concentration was initially given a value of 0% HCl and the diluted $FeCl_2$ was determined. The following series of calculations were made 7 times to arrive at the final concentrations. The number of repetitions could be reduced in number to 2 or 3 and still provide an accurate value but the computer time for calculations is not a limitation on the total process time.

The amount of $FeCl_2$ in diluted acid liquor was determined by subtracting the weight of water from the weight of the diluted sample and using a correction factor. The relationship may be stated as:

% $FeCl_2$ (diluted liquor) = (W2 − W3) × 5.22 − 0.51 × % HCl

For this example, this corresponds to = (1.83 − 0.16) × 5.22 − 0 = 8.72 % HCl (diluted liquor) = A + B × Corrected Conductivity + C × Corrected Conductivity$^2$, where A, B and C depend on % $FeCl_2$ and are determined from data in TABLE 1 using the slope of the lines from the general equation % $FeCl_2$ = A + B (Conductivity) + C (Conductivity)$^2$. TABLE 2 provides the coefficients for the conductivity at various levels of $FeCl_2$ derived from the quadratic relationships of the curves drawn through the data points. Similar curves may be generated for other acids and concentrations. The first approximation is generated for 8.72% $FeCl_2$ and an approximate A, B and C are determined by interpolation between the values shown. In the present example, the 8.72% $FeCl_2$ is used with the HCl coefficients for 0% $FeCl_2$ initially. The values for A, B and C are 0.0274, 0.08785 and 0.0008620 respectively. The first approximation calculation provides a value of 3.38% HCl in the diluted sample. The second approximation uses 3.38% HCl instead of 0 along with the appropriate coefficients. Repeating the calculation process approximation, a new $FeCl_2$ of 6.99% and a new HCl number of 3.31% is generated which is much closer to the real values. The greater the number of approximations the more accurate the value determinations. The 3-7 approximations were generated with the values remaining the same at 3.31 weight % HCl (diluted) and 7.03 weight % $FeCl_2$ (diluted). With computer processing, a series of 7 approximations may be completed in less than one second.

Since these calculations were for the diluted acid sample, the dilution factor must be considered to determine the bath concentrations of the liquor. The dilution factor is defined by the relationship of:

$$D.F. \text{ (dilution factor)} = (W1 - W3)/(W2 - W3)$$

For the present example, this D.F.=(4.59−0.16)/(1.83−0.16)=2.65 and allows us to calculate the undiluted concentrations by multiplying 2.65. This pickle liquor thus had an acid concentration of 2.65×3.31 wt. % which is equal to 8.78 grams HCl per 100 ml of liquor. Similarly, the wt. % $FeCl_2$ is 2.65×7.03 which is 18.64 grams $FeCl_2$ per 100 ml of liquor in the undiluted sample. The present method of analysis provides an accurate determination of acid concentration using the measured $FeCl_2$ in the diluted or weak acid range between about 1.5 wt % to about 4.5 wt % to approximate the acid concentration in a series of approximations until very accurate concentrations are determined. Preferably, the acid is in the range of about 1.5 to 4 wt % and more preferably about 2 to about 3 wt %.

The above analyzing system was computer controlled and sensor measurements were made by the computer. The dilution of the pickle liquor significantly reduced the influence of $FeCl_2$ on the conductivity reading and provided an accurate calculation of the grams HCl per 100 ml. While a coil having a 20 ml volume was weighed on an electronic balance to determine the density of the liquor, other means could be substituted for this step in the process. Other acids, such as sulfuric and nitric, may be analyzed. The present invention may be used for measuring various processing solutions, such as ammonium phosphate or other plating solutions.

Whereas the preferred embodiment has been described above for purpose of illustration, it will be apparent to those skilled in the art that numerous modifications may be made without departing from the spirit of the invention. The invention is therefore not limited by these specific embodiments but only to the extent set forth hereafter in the claims which follow.

We claim:
1. A method for determining acid concentration of an acid bath having a metal salt comprising the steps of:
   a) providing an acid sample from said acid bath;
   b) determining the density of said acid sample;
   c) diluting said acid sample with a dilution fluid to a level where said metal salt has substantially no influence on conductivity measurements;
   d) determining the density of said diluted acid sample;
   e) measuring the conductivity of said diluted acid sample; and
   f) determining said acid bath concentration from said density and said conductivity measurements.
2. The method of claim 1 including the step of correcting said conductivity measurements for temperature of said diluted acid sample.
3. The method of claim 1 wherein said dilution fluid is water.
4. The method of claim 1 wherein said acid bath is HCl and said metal salt is $FeCl_2$.
5. The method of claim 4 wherein said diluted HCl sample concentration is about 1.5 to about 4.5 grams HCl per 100 ml.
6. The method of claim 4 wherein said diluted HCl sample concentration is about 1.5 to about 4 grams HCl per 100 ml.
7. The method of claim 4 wherein said diluted HCl sample concentration is about 2 to about 3 grams HCl per 100 ml.
8. The method of claim 4 wherein 1 part of said HCl acid sample is diluted with about 1 to 2 parts dilution fluid for each part acid on a volume basis.
9. The method of claim 1 wherein said acid sample density is determined by weighing a fixed volume of said acid sample, diluting said acid sample, weighing said diluted acid sample of the same volume as said acid sample, weighing the same volume of dilution fluid as said diluted acid sample and said acid samples, said acid sample density determined using the relationship between said acid sample weight, said diluted acid sample weight and said dilution fluid weight.
10. The method of claim 1 wherein said acid sample is mixed prior to said acid sample density measurement to provide uniform temperature and composition.
11. The method of claim 1 wherein said acid bath determinations are controlled by a computer.
12. An apparatus for determining acid concentrations in an acid bath having a metal salt, said apparatus comprising:
   a) acid sampling means connectible to said acid bath to provide acid samples for determining said acid bath concentrations;
   b) acid sample pumping means connectible to said acid sampling means to regulate the flow of said acid samples through said apparatus;
   c) dilution fluid supply means;
   d) dilution fluid pumping means connectible to said dilution fluid supply means to provide said dilution fluid to said acid samples for forming diluted acid samples;
   e) mixing means connectible to said dilution fluid pumping means and said acid sample pumping means to improve uniformity of said acid samples and said diluted acid samples;
   f) acid density measuring means connectible to said mixing means to provide acid sample density measurements and diluted acid sample density measurements;
   g) diluted acid conductivity measuring means connectible to said pumping means to provide diluted acid conductivity measurements of said diluted acid sample;

h) diluted acid sample temperature measuring means connectible to said pumping means to provide diluted acid sample temperature measurements for correcting said diluted acid sample conductivity measurements; and i) processor means connectible to said density measuring means, said conductivity measuring means and said diluted acid sample temperature measuring means to determine said acid bath concentration from said acid sample density measurements, said diluted acid sample density measurements, said diluted acid conductivity measurements and said diluted acid temperature measurements.

13. The apparatus of claim 12 wherein means to determine % metal salt are included.

14. The apparatus of claim 12 wherein said acid is HCl.

15. An analyzing apparatus for determining the acid concentration of a sample of acid from an acid bath containing a metal salt, said apparatus comprising:

a) acid sampling means;

b) means to dilute said acid sample with a dilution fluid to provide a diluted acid concentration within a range where conductivity is not substantially influenced by said metal salts in said acid sample;

c) means to measure density of said acid, said diluted acid and said dilution fluid;

d) means to measure conductivity of said diluted acid; and e) means to determine acid concentration from said density and said conductivity measurements.

16. The apparatus of claim 15 wherein means to measure temperature of said acid sample are included.

17. The apparatus of claim 15 wherein sample mixing mixing means are included for mixing said acid samples and said diluted acid samples.

18. The apparatus of claim 15 wherein means to determine said metal salt concentrations in said acid sample are included.

19. An apparatus for automatic control of acid concentration in an acid bath having a metal salt, said apparatus comprising:

a) acid sampling means to provide acid samples from said acid bath;

b) acid sample pumping means to regulate flow of said acid samples through said apparatus;

c) dilution fluid supply means for said apparatus;

d) dilution fluid pumping means to supply said dilution fluid to said apparatus;

e) mixing means connected to both of said pumping means to mix said acid samples or to mix said dilution fluid with said acid samples to form diluted acid samples;

f) acid density measuring means to provide acid density measurements of said acid samples and said diluted acid samples;

g) a processor for controlling said acid concentrations in said acid bath using acid density measurements, diluted acid conductivity measurements and diluted acid temperature measurements.

h) means to transfer said acid density measurements and said diluted acid sample density measurements to said processor;

i) diluted acid sample conductivity measuring means to provide acid conductivity measurements of said diluted acid samples;

j) means to transfer said conductivity measurements to said processor;

k) diluted acid sample temperature measuring means to provide temperature measurements of said diluted acid samples for adjusting said conductivity measurements;

l) means to transfer said temperature measurements to said processor; and m) means to regulate acid additions to said acid bath in response to signals from said processor.

* * * * *